United States Patent

Ritson et al.

Patent Number: 5,851,179
Date of Patent: Dec. 22, 1998

[54] PULSE OXIMETER SENSOR WITH ARTICULATING HEAD

[75] Inventors: Carl Ritson, San Jose; Paul Mannheimer, Danville; Mitchell Levinson, Pleasanton; James R. Casciani, Cupertino, all of Calif.

[73] Assignee: Nellcor Puritan Bennett Incorporated, Pleasanton, Calif.

[21] Appl. No.: 728,658

[22] Filed: Oct. 10, 1996

[51] Int. Cl.[6] ............................................. A61B 5/00
[52] U.S. Cl. ................................................. 600/338
[58] Field of Search ........................ 128/633, 634, 128/664, 665; 600/310, 313, 322, 323, 338, 473, 476; 604/95

[56] References Cited

U.S. PATENT DOCUMENTS

| | | | |
|---|---|---|---|
| 4,898,577 | 2/1990 | Badger et al. | 604/95 |
| 5,231,989 | 8/1993 | Middleman et al. | 604/95 |
| 5,247,932 | 9/1993 | Chung et al. | 128/633 |
| 5,377,673 | 1/1995 | Van Dell et al. | 128/633 |
| 5,377,675 | 1/1995 | Ruskewicz et al. | 128/633 |
| 5,421,329 | 6/1995 | Casciani et al. | 128/633 |
| 5,665,477 | 9/1997 | Meathrel et al. | 428/500 |

FOREIGN PATENT DOCUMENTS

| | | |
|---|---|---|
| 0 471 898 A1 | 2/1992 | European Pat. Off. . |
| WO 97/17884 | 5/1998 | WIPO . |

*Primary Examiner*—Jennifer Bahr
*Assistant Examiner*—Eric F. Winakur
*Attorney, Agent, or Firm*—Townsend and Townsend and Crew LLP

[57] ABSTRACT

A fetal pulse oximeter sensor mounted on a sensor head with an articulating design. A lumen on one side of the sensor has a cable or rod therein to either push or pull that side of the sensor with respect to the main body, thus causing the sensor head to articulate. This can be used, for instance, to apply pressure against the fetus' scalp, with the sensor head, using the articulating mechanism, until an adhesive takes hold. Additionally, the sensor may be held in place on the fetus by an adhesive which is appropriate for a wet surface. The adhesive has the characteristics of having sufficient adhering characteristics to maintain the sensor in place, while at the same time not damaging the fetus' skin upon removal, without requiring suction.

11 Claims, 3 Drawing Sheets

PULSE OXIMETER SENSOR WITH ARTICULATING HEAD

BACKGROUND OF THE INVENTION

The present invention relates to a non-invasive pulse oximetry fetal intrauterine sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Known non-invasive sensors include devices that are secured to a portion of the body, such as a finger, ear or the scalp. In animals and humans, the tissue of these body portions is perfused with blood and the tissue surface is readily accessible to the clinician.

It is desirable that photoelectric pulse oximetry also be useful for monitoring the blood flow characteristics and constituents of a fetus. For example, monitoring fetal oxygen levels provides an effective way to detect and provide indications for treating hypoxia in the fetus during labor. However, known sensors adapted for use on infants or adults are not suited for intrauterine placement.

The environment in which the non-invasive intrauterine sensor must operate is fluid-filled (e.g., by amniotic fluid) and is only accessible through the restricted opening of the cervix. Visual inspection of the fetus and the sensor is likewise restricted. Moreover, the operating environment presents certain variants that interfere with detection of the fetal blood flow characteristics using known pulse oximetry techniques. For example, the presence of the waxy vernix caseosa, hair, mucus, blood and dead tissue cells on top of the fetal tissue surface against which the sensor is to be positioned create a problem in establishing contact between the optical components of the sensor and the surface of blood-perfused tissue. Detection of fetal blood flow characteristics by pulse oximetry is particularly complicated by the relatively low perfusion and low oxygen saturation of blood in fetal tissue. These environmental factors prevent known sensors from providing reliable information needed to calculate fetal blood characteristics.

It is known that positive attachment of a sensor to the tissue surface improves the quality of the photoelectric signal provided by the sensor. Positive attachment to a human's tissue may be obtained by vacuum, adhesives, tapes or devices such as clothespin-type clips. However, fetal tissue is relatively moist and there is limited access to the tissue surface. Consequently, conventional adhesives or tapes or clips are not adapted for intrauterine use.

There are two basic types of fetal sensors, presenting part sensors and beyond the presenting part sensors. "Presenting part" refers to the region of the fetus that, during labor, resides external to the cervical os. "Beyond the presenting part" falls within the uterus and extends out to the cervical os. Sensors beyond the presenting part can typically use the uterine wall to bias the sensor against the fetus. For the presenting part, however, the fetus' scalp is typically exposed to the open birth canal, and such biasing is not as readily available, with positive attachment usually being used.

Presenting Part Sensors

Known techniques for presenting part sensors include invasive attachment to fetal tissue, such as by a screw attachment penetrating the tissue, or vacuum attachment mechanisms.

Examples of presenting part sensors include U.S. Pat. No. 3,827,428 which discloses a heartbeat sensor using a coil screw for attaching to the fetus' scalp. Pulse oximeter and other sensors which use such a spiral or screw-type arrangement are also shown in U.S. Pat. Nos. 4,281,659; 4,658,825; 5,154,175; 5,361,757; 5,411,024; and German Published Application No. DE 4304691A1.

Examples of vacuum-type fetal sensors include that shown in U.S. Pat. No. 4,938,218 and PCT Published Application No. W091/15996, which shows a bellows for providing a low-pressure vacuum source. U.S. Pat. No. 4,537,197 shows another vacuum attachment fetal sensor.

A number of other designs are also known. U.S. Pat. No. 4,299,232 shows a combination of a suction adhesion with a suction-cup type attachment, in conjunction with an electrical pole which pierces the fetus' skin. U.S. Pat. No. 5,024,226 requires a bore hole in the brain of the patient. U.S. Pat. No. 4,543,965 uses an inflatable membrane to bias the sensor against the fetus at the presenting part.

U.S. Pat. No. 5,474,065, assigned to Graphic Controls Corporation discloses a probe with a suction cup shape and conductive hydrogel which is adhesive in a wet environment.

Non-Presenting Part Sensors

Other fetal sensors are designed to go beyond the presenting part. For instance, U.S. Pat. No. 5,247,932 shows a bladder between the fetus and the uterine wall which presses the active face of the sensor against the fetus' skin. U.S. Pat. No. 5,377,675 discloses a sensor using a fulcrum to bias the sensor against the fetus. PCT Published Application No. W091/07910 uses an inflatable sac to wedge the sensor against the fetus.

The intrauterine probe sensor must be safely and reliably deliverable to the point of contact with the fetus. It is desirable that intrauterine fetal monitoring be available early in labor, for example, to detect and treat hypoxia in the fetus during labor. Contact with the fetus can be made after natural rupture of the amniotic membrane by manually inserting a probe sensor into the uterus from the vagina, but access to the fetus through the vaginal canal is restricted by the cervix, which may be only slightly dilated to one or two centimeters when the membrane ruptures. Thus there is need for a fetal probe sensor that can be delivered to the fetus through a slightly dilated cervix, and a delivery system for doing so safely and reliably.

A presenting part sensor is often desirable for a variety of reasons. First, it is less invasive than a beyond the presenting part sensor. Second, a presenting part sensor may be used for spot-checking saturation rather than continuous monitoring. Third, a presenting part sensor may be necessary for monitoring fetus' located high in the uterus. Fourth, a presenting part sensor is easy to place and may be more reliably attached than a beyond-the-presenting part sensor.

SUMMARY OF THE INVENTION

The present invention provides an improved fetal pulse oximeter sensor which can be applied to the presenting part of a fetus or beyond the presenting part. The sensor may be held in place on the fetus' tissue by an adhesive which is appropriate for a wet surface, such as the fetus' scalp, cheek or torso. The adhesive has the characteristics of having sufficient adhering characteristics to maintain the sensor in place, while at the same time not damaging the fetus' skin upon removal. A flat or fetal conforming sensor surface is used, without requiring a suction cup shape.

In a preferred embodiment, the sensor is mounted on a sensor head with an articulating design. A lumen on one side of the sensor has a cable or rod therein to either push or pull that side of the sensor with respect to the main body, thus causing the sensor head to articulate. This can be used, for instance, to apply pressure against the fetus' scalp, with the sensor head, using the articulating mechanism, until the adhesive takes hold. Thereafter, the articulating mechanism can be relaxed or removed, leaving the sensor head in place. This eliminates the need for a suction cup used in the prior art. Alternatively, the articulating arm may be used to continuously hold the sensor head in place without the use of adhesives.

For a fuller understanding of the nature and advantages of the invention, reference should be made to the following description taken in conjunction with the accompanying drawings.

DESCRIPTION OF THE PREFERRED EMBODIMENT

Figure 1:
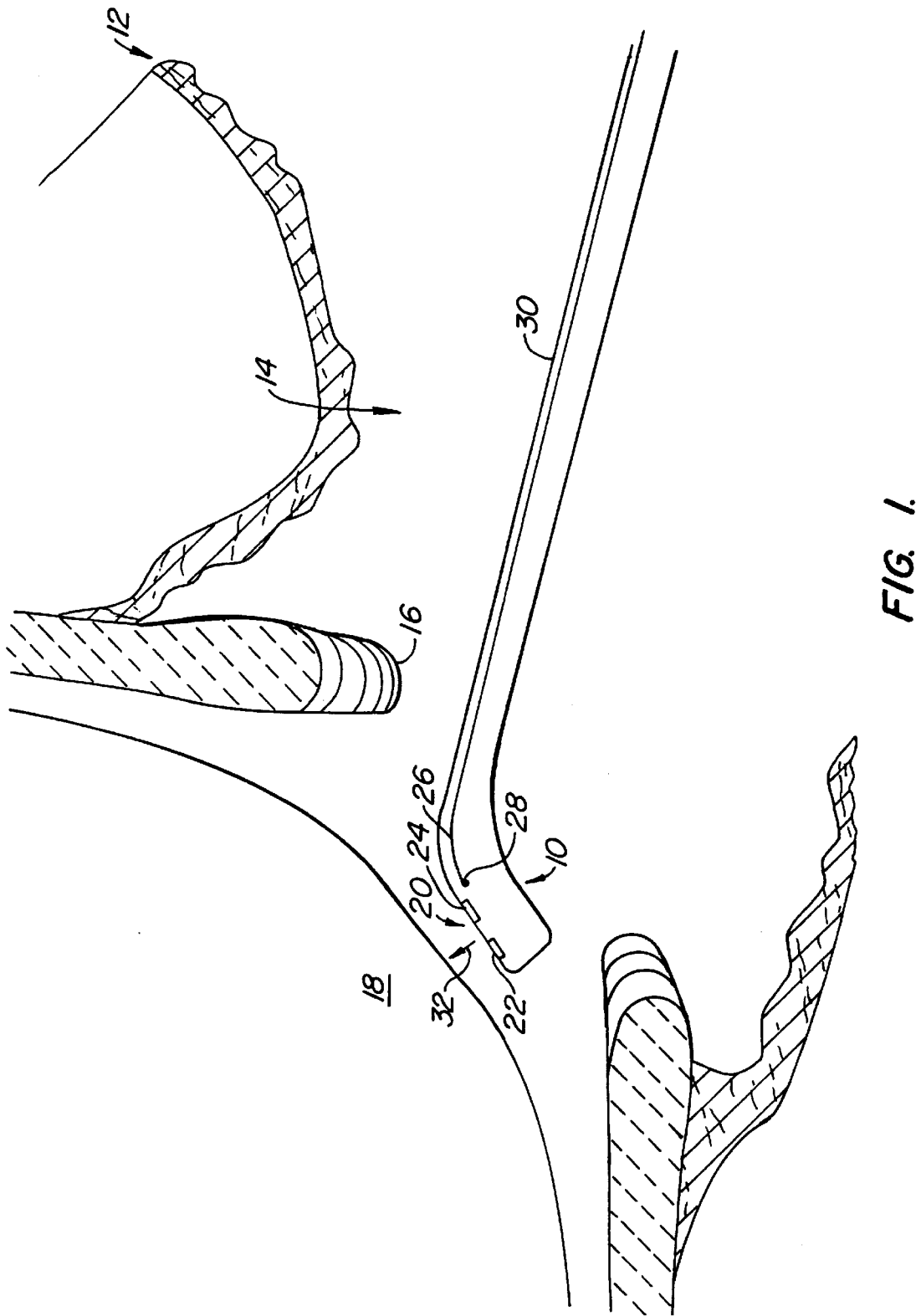
FIG. 1 is a diagram of one embodiment of a sensor according to the present invention inserted into a uterus.

FIG. 1 shows a sensor head 10 extending into a vagina 12, through a birth canal 14 and past the cervix 16 to become adjacent a fetus' head 18. The sensor has a face 20 with an emitter 22 and a photodetector 24. Also shown is a cable 26 attached to an anchor 28 running along one side of the sensor head and through a cable 30 extending out of the vagina.

Cable 26 can cause a sensor head to articulate, moving it in the direction towards the fetus' head as indicated by arrow 32.

Figure 2:
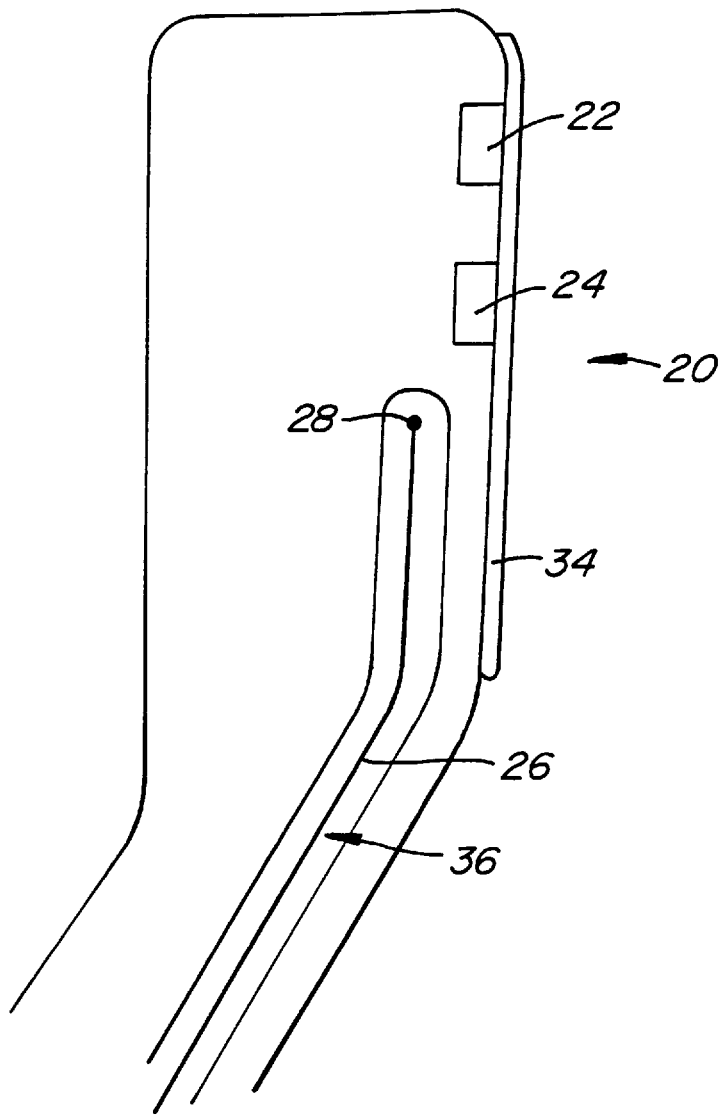
FIG. 2 is a cross-sectional view showing the articulating mechanism of one embodiment of the present invention.

Referring to FIG. 2, sensor face 20 is shown covered with an adhesive 34. The adhesive is a wet adhesive appropriate for sticking to a wet surface. At the same time, the adhesion force of the adhesive must not be so strong that it would cause the fetus' skin to tear, or become irritated, upon removal.

The use of an adhesive is practical for a presenting part sensor as a mechanism for anchoring a sensor in place. The presenting part typically is the fetus' scalp, and is removed from the eyes, nose or other sensitive parts where an adhesive might not be appropriate. In addition, such an adhesive could be used to hold the sensor in place beyond the presenting part, beyond the portion of the fetus' head engaged with the uterine wall, such as on the fetus' face or on the torso of the fetus further up in the uterus.

As shown in FIG. 2, the articulating mechanism comprises a cable 26 anchored by an anchor 28, which may, for instance, be a bar which extends out of the page in the cross-section of FIG. 2. The cable is disposed in a lumen, or channel, 36. As can be seen, lumen 36 is off to one side of the sensor head, the right side adjacent the sensor face 20 as shown in FIG. 2. When the cable is pulled, the sensor head will bend to the right in FIG. 2, since a force is being applied off-center to the sensor head. This will cause the sensor face 20 to move to the right and can be used to apply pressure to attach the adhesive on the sensor face to the fetus' head 18 and/or to hold the sensor in place against the fetus.

Figure 3:
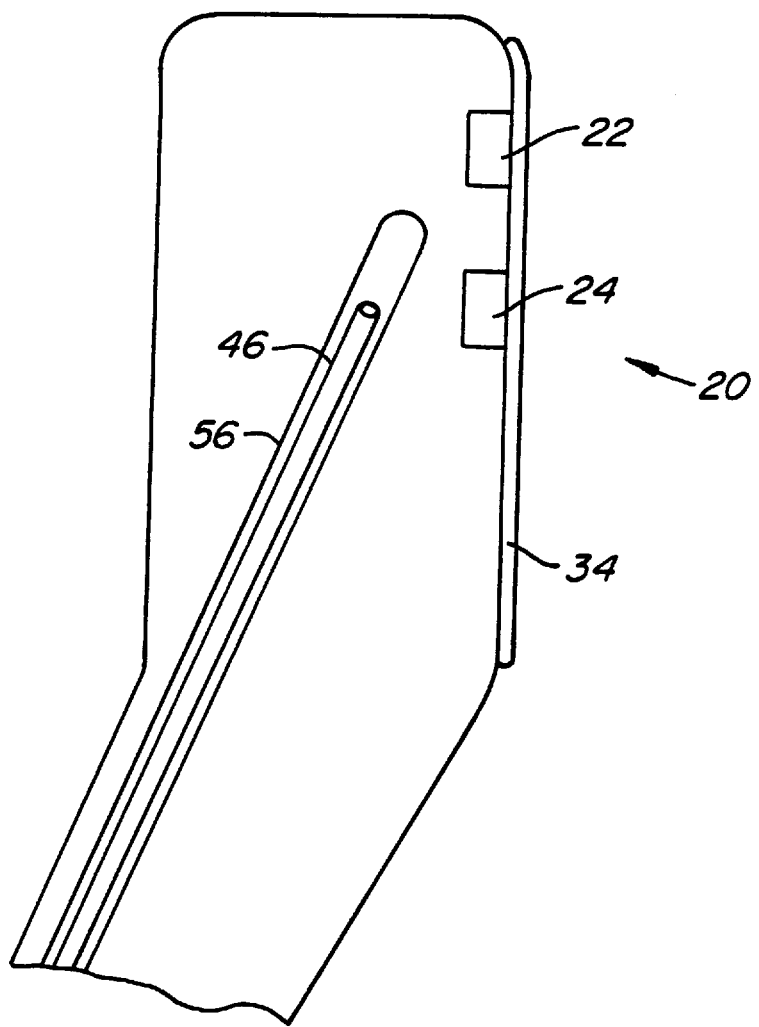
FIG. 3 is a cross-sectional view showing the articulating mechanism of another embodiment.

As shown in FIG. 3, in an alternate embodiment, a rod 46 can be used instead of cable 26, and can be placed without a lumen 56 on the other side of the sensor head 20. In such an embodiment, the rod 46 would be pushed to provide a forward force, thus causing the sensor head 20 to rotate away from the rod (as opposed to toward the cable and the embodiment of FIG. 2). Thus, such a rod could also be used to push the sensor head into the desired position against a fetus' head.

Cable 36 could be removable, so that after the head is articulated to the desired position, the cable can be released from anchor 28. This would be desirable to minimize the cables extending out of the vagina, limiting the cabling to the wires or fiber optics necessary for providing the emitter and detector functions. Such a release could be accomplished, for instance, by having a hook over a bar for the cable, with the cable being pushed to lift the hook over the bar, and then rotating it to remove the cable after the sensor head has been applied. The cable would need to have sufficient stiffness in order to accomplish this. A bar could have the same hooked end.

Alternately, multiple lumens could be provided in the sensor head, with multiple cables or bars or other mechanisms for providing the articulation in multiple directions. This would give additional control over the direction and placement of the sensor head.

As will be understood by those of skill in the art, the present invention may be embodied in other specific forms without departing from the spirit or essential characteristics thereof. For example, the articulating cable 26 could be a rip cord attachment to anchor 28, which, after use, with increased pressure, could be torn loose. Accordingly, the above description is intended to be illustrative, but not limiting, of the scope of the invention which is set forth in the following claims.

What is claimed is:

1. A perinatal pulse oximeter sensor for application to a fetus comprising:

a sensor head having a fetus engaging surface for engagement with said fetus;

light emitting means connected to said sensor head for emitting light of at least two wavelengths directed at said fetus;

light detecting means mounted in said sensor head for collecting light to be detected;

an articulating arm coupled to said sensor head for placement of said sensor head on said fetus; and means, connected to said articulating arm, for remotely controlling a degree of articulation over a plurality of angles and for providing a pressure on said sensor head.

2. A perinatal pulse oximeter sensor for application to a fetus comprising:

a sensor head having a fetus engaging surface for engagement with said fetus;

light emitting means connected to said sensor head for emitting light of at least two wavelengths directed at said fetus;

light detecting means mounted in said sensor head for collecting light to be detected; and an articulating arm coupled to said sensor head for placement of said sensor head on said fetus, wherein said articulating arm includes an elongate arm of flexible material having a lumen on one side off-center;

an anchoring member adjacent an end of said lumen near said sensor head; and an activating member attached to said anchoring member and extending out an end of said lumen opposite said sensor head, said activating member providing a pressure on said sensor head.

3. The sensor of claim 2 wherein said activating member is a cable.

4. A perinatal pulse oximeter sensor for application to a fetus comprising:

a sensor head having a fetus engaging surface for engagement with said fetus;

light emitting means connected to said sensor head for emitting light of at least two wavelengths directed at said fetus;

light detecting means mounted in said sensor head for collecting light to be detected;

an articulating arm coupled to said sensor head for placement of said sensor head on said fetus;

means, connected to said articulating arm, for remotely controlling a degree of articulation over a plurality of angles; and a wet surface adhesive attached to said fetus engaging surface.

5. A perinatal pulse oximeter sensor for application to a fetus comprising:

a sensor head having a substantially flat fetus engaging surface for engagement with said fetus;

light emitting means connected to said sensor head for emitting light of at least two wavelengths directed at said fetus;

light detecting means mounted in said sensor head for collecting light to be detected;

a wet surface adhesive attached to said fetus engaging surface; and an articulating arm coupled to said fetus' head for placement of said sensor head on said fetus, wherein said articulating arm includes an elongate arm of flexible material having a lumen on one side off-center;

an anchoring member adjacent an end of said lumen near said sensor head; and an activating member attached to said anchoring member and extending out an end of said lumen opposite said sensor head.

6. The sensor of claim 5 wherein said activating member is a cable.

7. The sensor of claim 5 wherein said activating member is a rod.

8. A method for applying a perinatal pulse oximeter sensor to a fetus and measuring blood oxygen saturation, comprising the steps of:

providing a sensor head having a substantially flat fetus engaging surface;

engaging said engaging surface with said fetus;

attaching said fetus engaging surface to said fetus with a wet surface adhesive;

articulating said sensor head to provide pressure against said fetus until said wet surface adhesive takes hold;

emitting from said sensor head light of at least two wavelengths directed at said fetus; and collecting light to be detected in said sensor head.

9. The method of claim 8 wherein said sensor is attached to a presenting part of said fetus.

10. The method of claim 8 wherein said sensor is attached to a portion of said fetus beyond the presenting part.

11. A perinatal pulse oximeter sensor for application to a fetus comprising:

a sensor head having a fetus engaging surface for engagement with said fetus;

light emitting means connected to said sensor head for emitting light of at least two wavelengths directed at said fetus;

light detecting means mounted in said sensor head for collecting light to be detected; and an articulating arm coupled to said sensor head for placement of said sensor head on said fetus, wherein said articulating arm includes an elongate arm of flexible material having a lumen on a side off-center and opposite said sensor head; and a rod disposed within said lumen and extending out an end of said lumen opposite said sensor head, said rod providing a pressure on said sensor head.

\* \* \* \* \*